United States Patent
Zurakhov et al.

(10) Patent No.: US 12,352,905 B2
(45) Date of Patent: Jul. 8, 2025

(54) REDUCING ELECTROMAGNETIC NOISE IN ULTRASOUND SIGNALS

(71) Applicant: BIOSENSE WEBSTER (ISRAEL) LTD., Yokneam (IL)

(72) Inventors: Grigoriy Zurakhov, Haifa (IL); Meir Bar-Tal, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 293 days.

(21) Appl. No.: 18/195,989

(22) Filed: May 11, 2023

(65) Prior Publication Data

US 2024/0377516 A1    Nov. 14, 2024

(51) Int. Cl.
| | | |
|---|---|---|
| *A61B 8/12* | (2006.01) | |
| *A61B 8/00* | (2006.01) | |
| *G01S 7/52* | (2006.01) | |

(52) U.S. Cl.
CPC ............ *G01S 7/52077* (2013.01); *A61B 8/12* (2013.01); *A61B 8/4494* (2013.01); *A61B 8/5269* (2013.01)

(58) Field of Classification Search
CPC .................................................. A61B 8/5269
See application file for complete search history.

(56) References Cited

U.S. PATENT DOCUMENTS

| | | |
|---|---|---|
| 5,391,199 A | 2/1995 | Ben-Haim |
| 5,443,489 A | 8/1995 | Ben Haim |
| 5,558,091 A | 9/1996 | Acker |
| 6,172,499 B1 | 1/2001 | Ashe |
| 6,239,724 B1 | 5/2001 | Doron |
| 6,332,089 B1 | 12/2001 | Acker |
| 6,484,118 B1 | 11/2002 | Govari |
| 6,618,612 B1 | 9/2003 | Acker |
| 6,690,963 B2 | 2/2004 | Ben Haim |
| 6,788,967 B2 | 9/2004 | Ben Haim |

(Continued)

FOREIGN PATENT DOCUMENTS

| | | |
|---|---|---|
| EP | 3282951 A1 | 2/2018 |
| JP | 2009261441 A | 11/2009 |

OTHER PUBLICATIONS

European Search Report for corresponding EPA No. 24175152.8 dated Sep. 20, 2024.

*Primary Examiner* — Ashley K Buran
*Assistant Examiner* — Tommy T Ly

(57) ABSTRACT

A system for use with ultrasound transducers on a catheter and connected to different respective channels includes circuitry and a processor. The circuitry is configured to receive a signal, which includes transduction of ultrasound reflections, over any given one of the channels, and to receive respective noise-signals, which include less transduction of ultrasound reflections than the signal, over a group of others of the channels. The processor is configured to receive the signal and the noise-signals from the circuitry, and to reduce noise in the signal, by, based on the noise-signals, computing, for the given channel, one or more noise-estimation functions, each of which is applicable to a respective subset of the noise-signals so as to return an estimate of noise received over the given channel while the subset of the noise-signals were received, using the noise-estimation functions, computing an estimated-noise signal, and subtracting the estimated-noise signal from the signal.

26 Claims, 9 Drawing Sheets

(56) References Cited

U.S. PATENT DOCUMENTS

| | | |
|---|---|---|
| 6,892,091 B1 | 5/2005 | Ben Haim |
| 7,536,218 B2 | 5/2009 | Govari |
| 7,756,576 B2 | 7/2010 | Levin |
| 7,848,787 B2 | 12/2010 | Osadchy |
| 7,869,865 B2 | 1/2011 | Govari |
| 8,456,182 B2 | 6/2013 | Bar-Tal |
| 8,998,812 B2 | 4/2015 | Ziv-Ari |
| 9,700,284 B2 | 7/2017 | Kapoor |
| 2008/0114254 A1* | 5/2008 | Matcovitch ......... G01S 15/8968 600/463 |
| 2012/0065509 A1* | 3/2012 | Ziv-Ari ............... G01S 7/52077 600/443 |
| 2016/0113699 A1 | 4/2016 | Sverdlik |
| 2017/0071578 A1 | 3/2017 | Srinivasan et al. |

* cited by examiner

REDUCING ELECTROMAGNETIC NOISE IN ULTRASOUND SIGNALS

FIELD OF THE INVENTION

The present disclosure is related in general to the field of signal processing, and in particular to the processing of ultrasound signals.

BACKGROUND OF THE INVENTION

An ultrasound transducer generates ultrasound waves by converting electrical signals to mechanical energy, and converts reflections of the waves back to electrical signals.

BRIEF DESCRIPTION OF THE DRAWINGS

The present disclosure will be more fully understood from the following detailed description of examples thereof, taken together with the drawings, in which.

DETAILED DESCRIPTION

Overview

Figure 1:
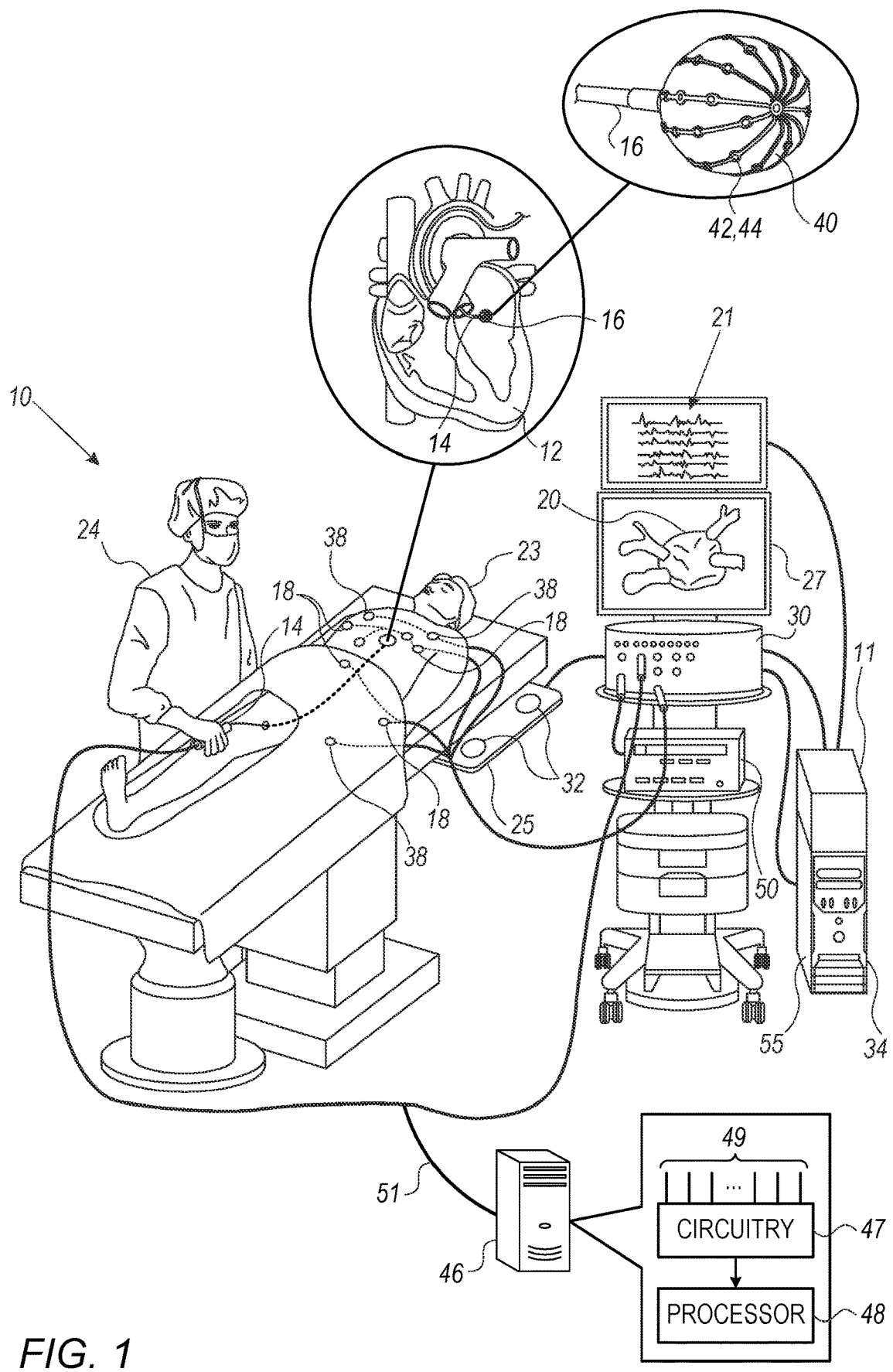
FIG. 1 is a schematic illustration of an example electrophysiology mapping and ablation system, in accordance with some examples of the present disclosure.

In some procedures, an ultrasound catheter comprising multiple ultrasound transducers is inserted into the body of a subject. Subsequently, the transducers transmit ultrasound waves and receive reflections of these waves from tissue of the subject. In response to these reflections, the transducers generate electrical signals, which are received over different respective channels and may be processed, for example, so as to estimate a parameter (e.g., a thickness or elasticity) of the subject's tissue, and/or to produce an image and/or anatomical map of the tissue.

A challenge, when performing such a procedure, is that nearby electrical components may generate electromagnetic noise, which is superimposed onto the electrical signals.

To address this challenge, the present inventors cleverly capitalized on two observations:

1) The noise on any one channel is often correlated with the noise on other channels, varying only in amplitude and/or phase.
2) In many cases, while a signal is received over one channel, at least some of the other channels carry "noise-signals," which include noise but do not include any substantial transduction of ultrasound reflections. For example, the ultrasound transducers may be disposed on a convex surface (e.g., a balloon, such as an ellipsoidal balloon), rather than being distributed over a two-dimensional array. Alternatively or additionally, the distance between two ultrasound transducers may be relatively large, e.g., more than ten times the wavelength of the transmitted waves. Alternatively or additionally, the transmitted beams may be relatively narrow. By virtue of the convexity of the surface, the distance between transducers, and/or the narrowness of the beams, there may be relatively little overlap in the respective fields-of-view of the transducers.

More specifically, based on these two observations, the present inventors realized that it is possible, using a computer processor, to learn the manner in which the noise on any given channel is correlated with the noise on other channels. Subsequently, given a noisy signal received over the given channel and one or more noise-signals received, simultaneously, over the other channels, the processor may estimate the noise on the given channel, based on the noise-signals and the learned correlation. The processor may then subtract this estimated noise from the signal.

In some examples of the present disclosure, the processor learns the correlation in a first stage of execution, based on simultaneously-received first noise-signals received over the given channel and one or more other channels. Subsequently, in a second stage of execution, the processor removes noise from the signal, based on the learned correlation and second noise-signals received, over the other channels, while the signal is received.

In other examples, the processor uses only a single set of noise-signals, which are received over the other channels while the signal is received over the given channel. In particular, the processor identifies portions of the signal that do not appear to include any substantial amount of transduction of ultrasound reflections. Based on these portions and corresponding portions of the noise-signals, the processor learns the correlation. Subsequently, the processor removes noise from the signal, based on the learned correlation and the noise-signals.

In some examples, the processor computes a linear time-invariant (LTI) model that describes the correlation between the channels. In particular, for any given one of the channels, the processor may compute an impulse-response vector, which describes the noise on the given channel as a function of the noise on one or more other channels. This impulse-response vector may then be used to compute the estimated noise on the given channel.

For greater efficiency, some examples of the present disclosure capitalize on the geometry of the catheter so as to facilitate receiving simultaneous signals over different respective channels, and/or receiving a noise-signal for use in estimating the noise over a first channel while receiving a signal over a second channel. Alternatively or additionally, this optimization may be achieved by virtue of a property (e.g., frequency) of the transmission varying between ultrasound transducers.

System Description

Reference is initially made to FIG. 1, which is a schematic illustration of an example electrophysiology mapping and ablation system 10, in accordance with some examples of the present disclosure. One commercial product embodying elements of system 10 is available as the CARTO™ 3 System, available from Biosense Webster, Inc., 31A Technology Drive, Irvine, CA 92618.

System 10 comprises one or more catheters, which are percutaneously inserted by a physician 24 into the body of a subject 23. Following the insertion of each catheter, physician 24 navigates the catheter through the vascular system of subject 23 into a chamber or vascular structure of the subject's heart 12. Typically, the catheters are navigated through a delivery sheath 14. The catheters may include a catheter for sensing signals, such as intracardiac electrogram (IEGM) signals, from cardiac tissue, a catheter for ablating cardiac tissue, and/or a catheter for both sensing and ablating.

Typically, each catheter comprises a tracking sensor for tracking the three-dimensional (3D) location and orientation of the distal end of the catheter. Typically, the tracking sensor comprises three magnetic coils. A location pad 25, which comprises a plurality of magnetic coils 32 configured to generate a magnetic field in a predefined working volume, is positioned near (e.g., underneath) subject 23. Based on signals induced in the coils by the magnetic field, the location and orientation of the distal end of the catheter is tracked. Details of such magnetic-based tracking are described in U.S. Pat. Nos. 5,5391,199, 5,443,489, 5,558,091, 6,172,499, 6,239,724, 6,332,089, 6,484,118, 6,618,612, 6,690,963, 6,788,967, and 6,892,091.

Typically, system 10 further comprises one or more electrode patches 38 configured to contact the skin of subject 23. Patches 38 may establish a location reference for location pad 25. Additionally, electrical current from electrodes disposed on any of the catheters may be sensed at patches 38, and the location of each electrode may be triangulated in response thereto. This location information may be combined with the information derived from the magnetic-based tracking described above so as to increase the precision of the tracking of the catheter. Details of such impedance-based tracking technology are described in U.S. Pat. Nos. 7,536,218, 7,756,576, 7,848,787, 7,869,865, and 8,456,182.

System 10 further comprises a recorder 11 and a display 27. Recorder 11 is configured to record electrocardiographic (ECG) signals 21 acquired by body-surface ECG electrodes 18 and/or IEGM signals acquired by an intrabody catheter, and optionally, to display these signals on display 27. Recorder 11 may also be configured to pace heart 12 and/or may be electrically connected to a standalone pacer.

System 10 further comprises an ablation-energy generator 50 configured to conduct ablative energy to one or more electrodes at the distal end of an ablation catheter. Energy produced by ablation-energy generator 50 may include, but is not limited to, radiofrequency (RF) energy and/or pulsed field ablation (PFA) energy, including monopolar or bipolar high-voltage direct-current (DC) pulses for effecting irreversible electroporation, or combinations thereof. Ablation-energy generator 50 comprises energy-generating circuitry configured to produce the energy, along with a controller configured to control the circuitry and, optionally, to perform other computational functions.

System 10 further comprises a workstation 55 comprising a processor 34, a volatile memory and/or non-volatile memory that may store appropriate software instructions and/or data, and a user interface. Processor 34 may be configured to perform multiple functions, including, for example, (1) mapping the endocardial anatomy of heart 12 in 3D and rendering the resulting anatomical map 20 for display on display 27, (2) displaying, on display 27, activation sequences and/or other data compiled from ECG signals 21 in representative visual indicia or imagery superimposed on anatomical map 20, (3) displaying the real-time location and orientation of one or more catheters within the body of subject 23, and (4) displaying sites of interest, such as sites at which ablation energy has been applied.

System 10 further comprises a patient interface unit (PIU) 30, which is configured to establish electrical communication between power supplies, workstation 55, and the electrophysiological equipment belonging system. The electrophysiological equipment may comprise, for example, one or more catheters, location pad 25, ECG electrodes 18, electrode patches 38, ablation-energy generator 50, and/or recorder 11. Typically, PIU 30 further comprises another processor configured to compute the location and orientation of each of the catheters and to perform any relevant computations based on ECG signals 21.

In some examples, at least one of the catheters is an ultrasound catheter 16, on which multiple ultrasound transducers 44 are disposed. Ultrasound transducers 44 are connected to different respective (wired) channels 49, which run to the proximal end of catheter 16. Electrical signals, which include both the transduction of ultrasound reflections from tissue of subject 23 and electromagnetic noise, are received, over channels 49, by circuitry 47. Typically, circuitry 47 comprises an anti-aliasing filter, which restricts the bandwidth of the signals, analog-to-digital (A/D) conversion circuitry, configured to digitize the electrical signals, and noise-filtration circuitry, configured to remove some of the noise from the signals. A processor 48 is configured to receive the signals (typically in digital form) from circuitry 47, and to process the signals as described in detail below with reference to the subsequent figures. The output of this processing may be communicated to processor 34, which may use this output to facilitate the construction of anatomical map 20 and/or to display ultrasound images on display 27.

Typically, circuitry 47 and processor 48 are situated in an ultrasound unit 46, which is connected, via a cable 51, to catheter 16.

In the example shown in FIG. 1, catheter 16 comprises a balloon 40 and multiple sensing units 42 disposed on balloon 40. Each sensing unit 42 comprises an ultrasound transducer 44 and, optionally, an electrode for acquiring IEGM signals. As described above, each transducer is connected, via one or more wires passing through catheter 16, to circuitry 47. Each electrode is connected, via one or more other wires passing through catheter 16, to PIU 30.

In other examples, catheter 16 comprises a plurality of splines (e.g., in a basket formation), or any other structure suitable for supporting ultrasound transducers 44.

As described above in the Overview, various components of system 10, such as PIU 30, may generate electromagnetic noise that is superimposed on the signals received from transducers 44, and cannot be entirely removed by circuitry 47. Typically, processor 48 is configured to reduce this noise, as described in detail below with reference to the subsequent figures. Alternatively, this noise-reduction function may be performed by another processor belonging to system 10, such as processor 34 or the processor of PIU 30. As yet another alternative, this function may be performed cooperatively by multiple processors belonging to system 10. Thus, it should be understood that the term "the processor," as used below, may refer to any single processor or group of multiple processors belonging to system 10.

In general, the functionality of each of the processors described herein may be implemented solely in hardware, e.g., using one or more fixed-function or general-purpose integrated circuits, Application-Specific Integrated Circuits (ASICs), and/or Field-Programmable Gate Arrays (FPGAs). Alternatively, this functionality may be implemented at least partly in software. For example, the processor may be embodied as a programmed processor comprising, for example, a central processing unit (CPU) and/or a Graphics Processing Unit (GPU). Program code, including software programs, and/or data may be loaded for execution and processing by the CPU and/or GPU. The program code and/or data may be downloaded to the processor in electronic form, over a network, for example. Alternatively or additionally, the program code and/or data may be provided and/or stored on non-transitory tangible media, such as magnetic, optical, or electronic memory. Such program code and/or data, when provided to the processor, produce a machine or special-purpose computer, configured to perform the tasks described herein.

Noise Reduction

Figure 2:
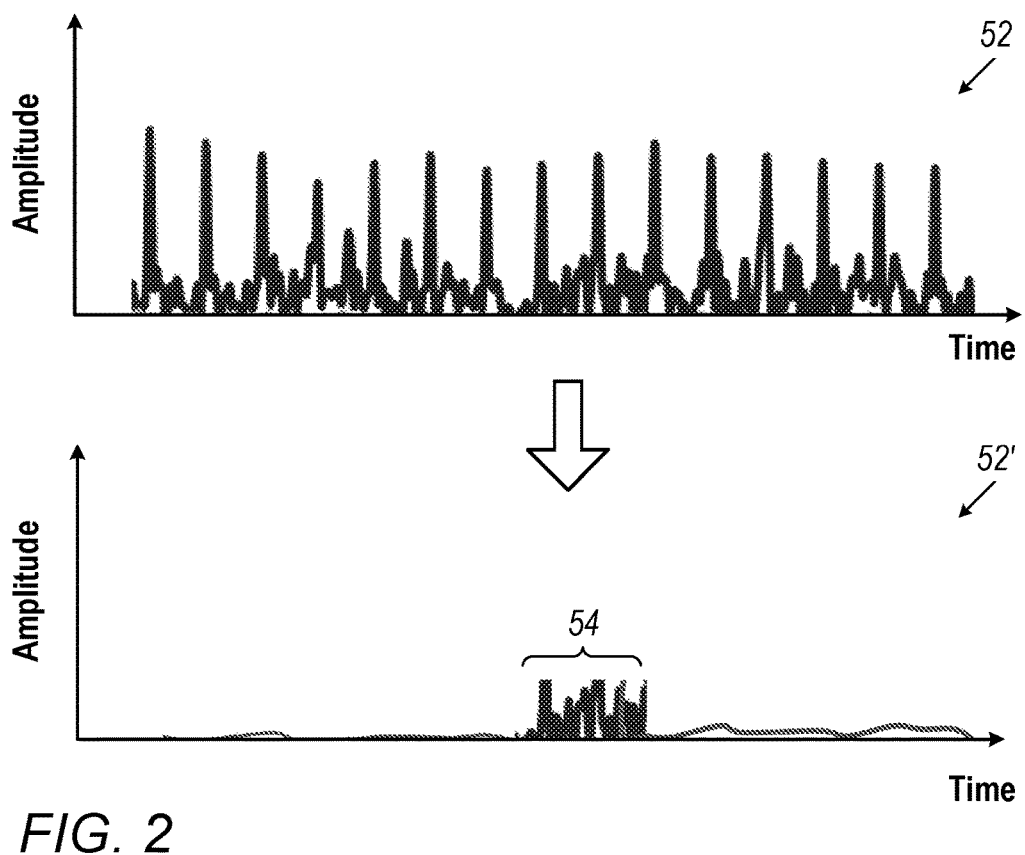
FIG. 2 is a schematic illustration of a removal of noise from a signal, in accordance with some examples of the present disclosure.

Reference is now made to FIG. 2, which is a schematic illustration of a removal of noise from a signal 52, in accordance with some examples of the present disclosure. (Notwithstanding the fact that, for ease of illustration, the present figures use a signal envelope to depict each signal, it is noted that the signal processing described herein is typically performed on the original signals received from circuitry 47 (FIG. 1), which typically include radiofrequency oscillations within the signal envelopes.)

As described above with reference to FIG. 1, signal 52, which includes a transduction 54 of ultrasound reflections, may be received, by circuitry 47, over any given one of channels 49. Further to receiving signal 52 from the circuitry, the processor reduces noise in the signal. In particular, the processor uses one or more noise-estimation functions to compute an estimated-noise signal, and then subtracts the estimated-noise signal from signal 52, thus obtaining a less-noisy signal 52'.

As further described below, the processor computes the one or more noise-estimation functions for the given channel based on one or more noise-signals, which are received over others of channels 49 and include less transduction of ultrasound reflections than does signal 52. Each of the noise-estimation functions is applicable to a respective subset of the noise-signals so as to return an estimate of noise received over the given channel while the subset of the noise-signals were received. For example, the processor may compute a single noise-estimation function, which is applicable to all of the noise-signals (i.e., the aforementioned subset is not necessarily a strict subset). Alternatively, for example, the number of noise-estimation functions may be the same as the number of noise-signals, each noise-estimation function being applicable to a different respective one of the noise-signals.

I. Two-Stage Technique

In some examples, the processor executes the aforementioned functionality in two stages, using two different sets of noise-signals. In particular, one or more "first noise-signals," which are simultaneously received, respectively, from the given channel and from one or more other channels, are used to compute the noise-estimation functions. The noise-estimation functions are then applied to one or more "second noise-signals," which are received, while signal 52 is received, from the same other channels, so as to compute the estimated-noise signal.

Each of these stages is hereby described in detail.

(i) First Stage—Computing the Noise-Estimation Functions

Figure 3:
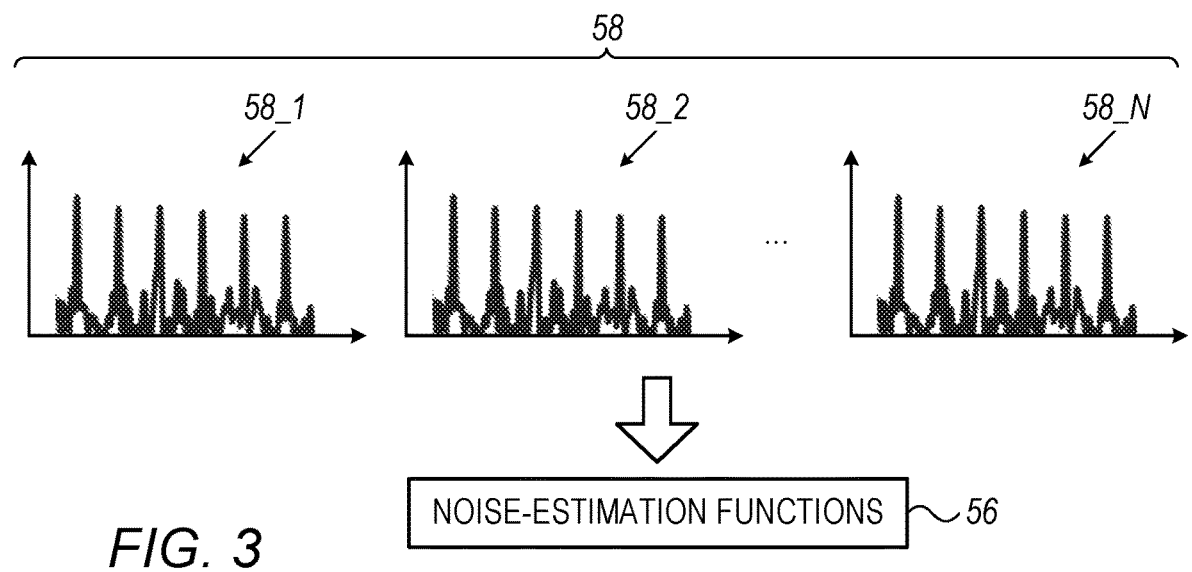
FIG. 3 is a schematic illustration of a technique for computing one or more noise-estimation functions, in accordance with some examples of the present disclosure.

Reference is now made to FIG. 3, which is a schematic illustration of a technique for computing one or more noise-estimation functions 56 from first noise-signals 58, in accordance with some examples of the present disclosure.

As illustrated in FIG. 3, respective first noise-signals 58_1, 58_2, . . . 58_N are received, simultaneously, over N of the channels. (Typically, first noise-signals 58 do not include any transduction of ultrasound reflections.) Based on first noise-signals 58, the processor computes one or more noise-estimation functions 56 for at least one of the N channels. For example, the processor may compute N sets of one or more noise-estimation functions, each set of noise-estimation functions being for use in reducing noise received over a different respective one of the N channels.

In some examples, the first noise-signals are received before the catheter enters the body of the subject, during a calibration procedure. In other examples, the first noise-signals are received while the catheter is inside the body of the subject, e.g., immediately before the transduction of ultrasound reflections begins. In yet other examples, the first noise-signals are received after signal 52 (FIG. 2) is received over at least one of the channels, while the catheter is inside or outside the body. For example, the processor may divide a signal received over one of the channels into two portions: (a) signal 52, which includes a transduction of ultrasound reflections, and (b) a first noise-signal following signal 52, which is known not to include any such transduction. Other options for the receipt of the first noise-signals are described below with reference to FIG. 11.

Figure 4:
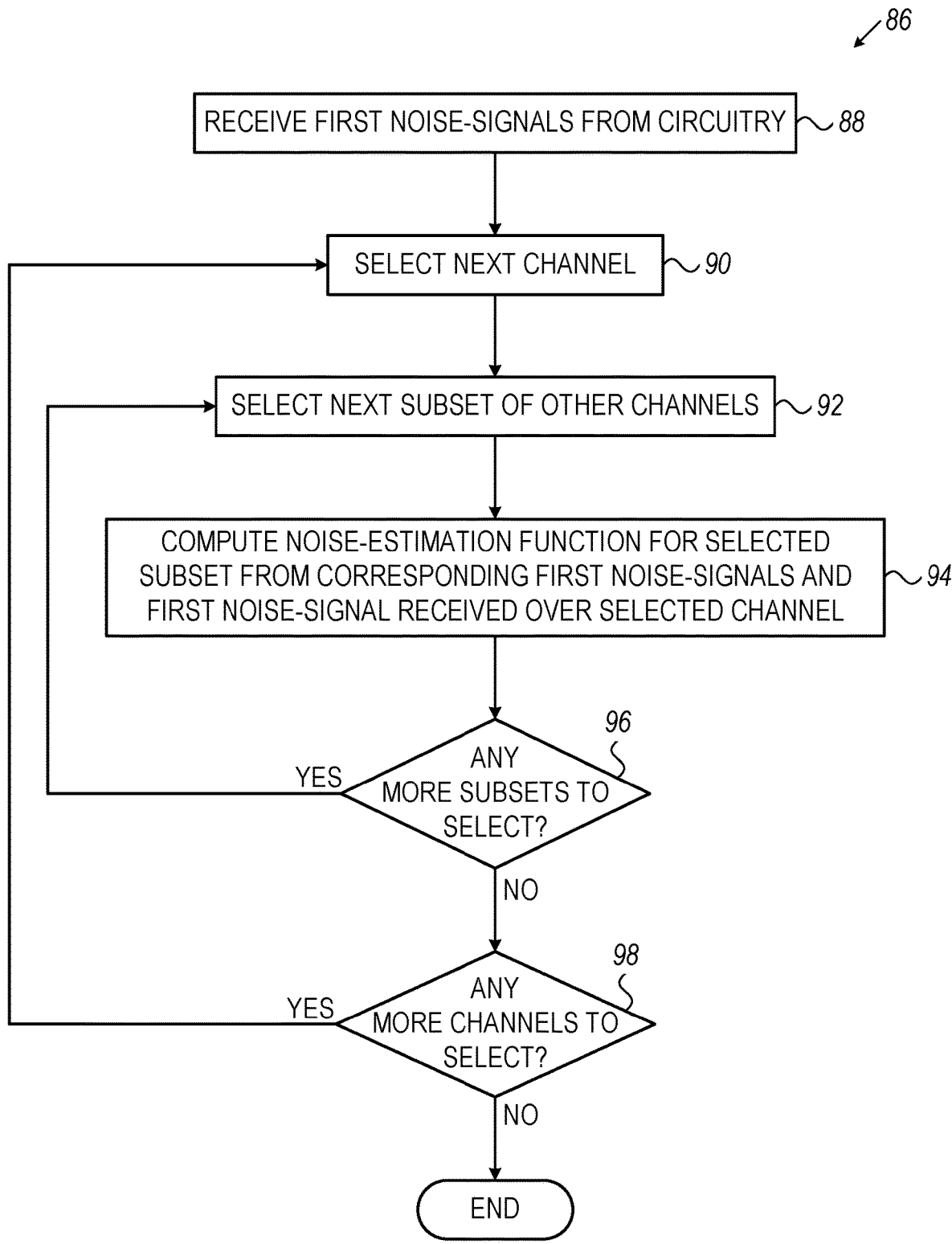
FIG. 4 is a flow diagram for an algorithm for computing one or more noise-estimation functions, in accordance with some examples of the present disclosure.

For example implementation of this functionality, reference is now additionally made to FIG. 4, which is a flow diagram for an algorithm 86 for computing one or more noise-estimation functions, in accordance with some examples of the present disclosure.

Algorithm 86 begins with a signal-receiving step 88, at which the processor receives first noise-signals 58, which were received simultaneously over different respective channels, from the circuitry. Following signal-receiving step 88, the processor selects one of the channels at a channel-selecting step 90.

Next, the processor computes one or more noise-estimation functions, each of which is configured to estimate the noise received over the selected channel based on the noise received over a different respective subset of the other channels over which the first noise-signals were received. The processor selects each such subset at a subset-selecting step 92. Next, at a function-computing step 94, the processor computes the noise-estimation function for the selected subset (i.e., the noise-estimation function that takes, as input, the noise received over the selected subset of channels) from the corresponding first noise-signals (i.e., the first noise-signals received over the subset of channels) and the first noise-signal received over the selected channel. Following the computation, the processor checks, at a checking step 96, whether any more subsets of channels remain for selection. If yes, the processor returns to subset-selecting step 92.

In some examples, the processor computes only a single noise-estimation function, and thus selects only a single subset, for a selected channel.

Upon ascertaining, at checking step 96, that no unselected subsets remain, the processor checks, at another checking step 98, whether any channels remain for selection. If yes, the processor returns to channel-selecting step 90. Otherwise, the execution of algorithm 86 ends.

(ii) Second Stage—Removing Noise

Figure 5:
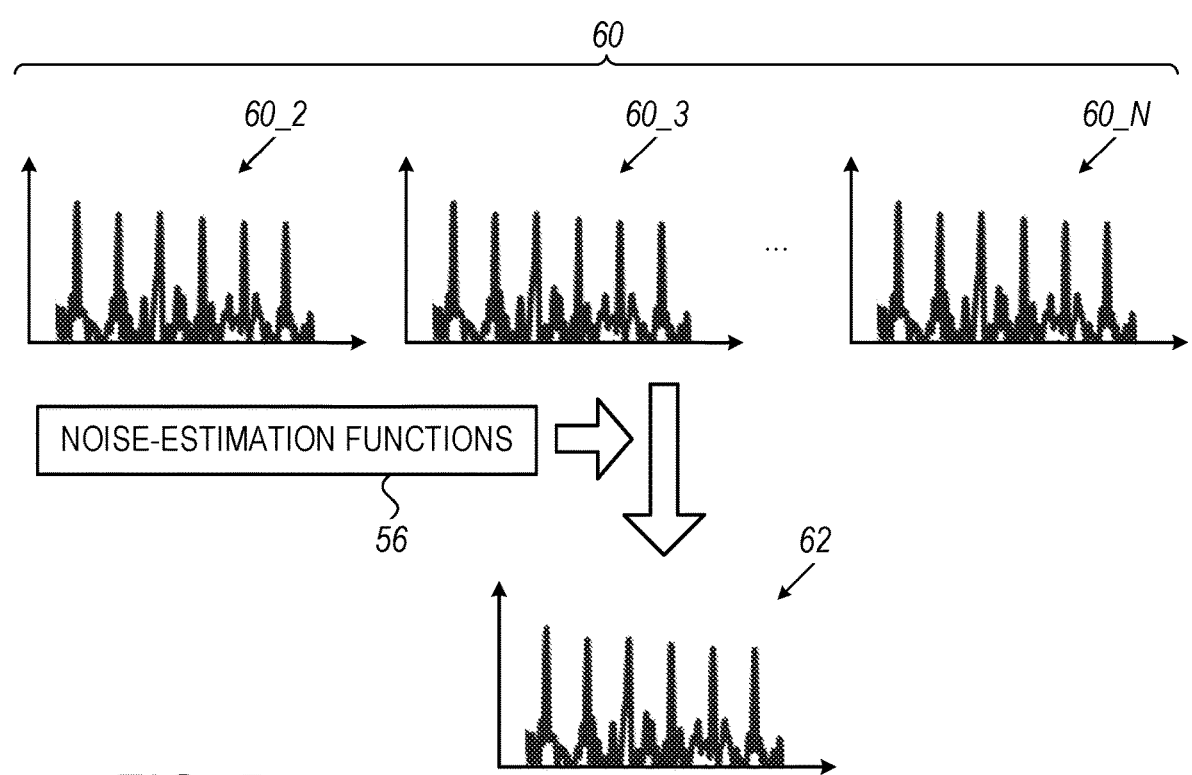
FIG. 5 is a schematic illustration of a computation of an estimated-noise signal, in accordance with some examples of the present disclosure.

Reference is now made to FIG. 5, which is a schematic illustration of a computation of an estimated-noise signal 62, in accordance with some examples of the present disclosure.

By way of example, FIG. 5 shows the computation of estimated-noise signal 62 for the first of N channels, based on second noise-signals 60 received over the second through $N^{th}$ channels while signal 52 (FIG. 2) was received over the first channel. In particular, to compute the estimated-noise signal, the processor applies, to second noise-signals 60_2, 60_3, . . . 60_N, the one or more noise-estimation functions that were computed for the first channel. Subsequently, as described above with reference to FIG. 2, the processor uses the estimated-noise signal to reduce the noise in the signal received over the first channel.

The second noise-signals typically include, at most, only a small amount of transduction of ultrasound reflections. For example, for each of the second noise-signals, the energy of the noise in the signal may exceed the energy of any ultrasound reflections in the signal, e.g., by a factor of at least five, such as a factor of at least ten.

Figure 6:
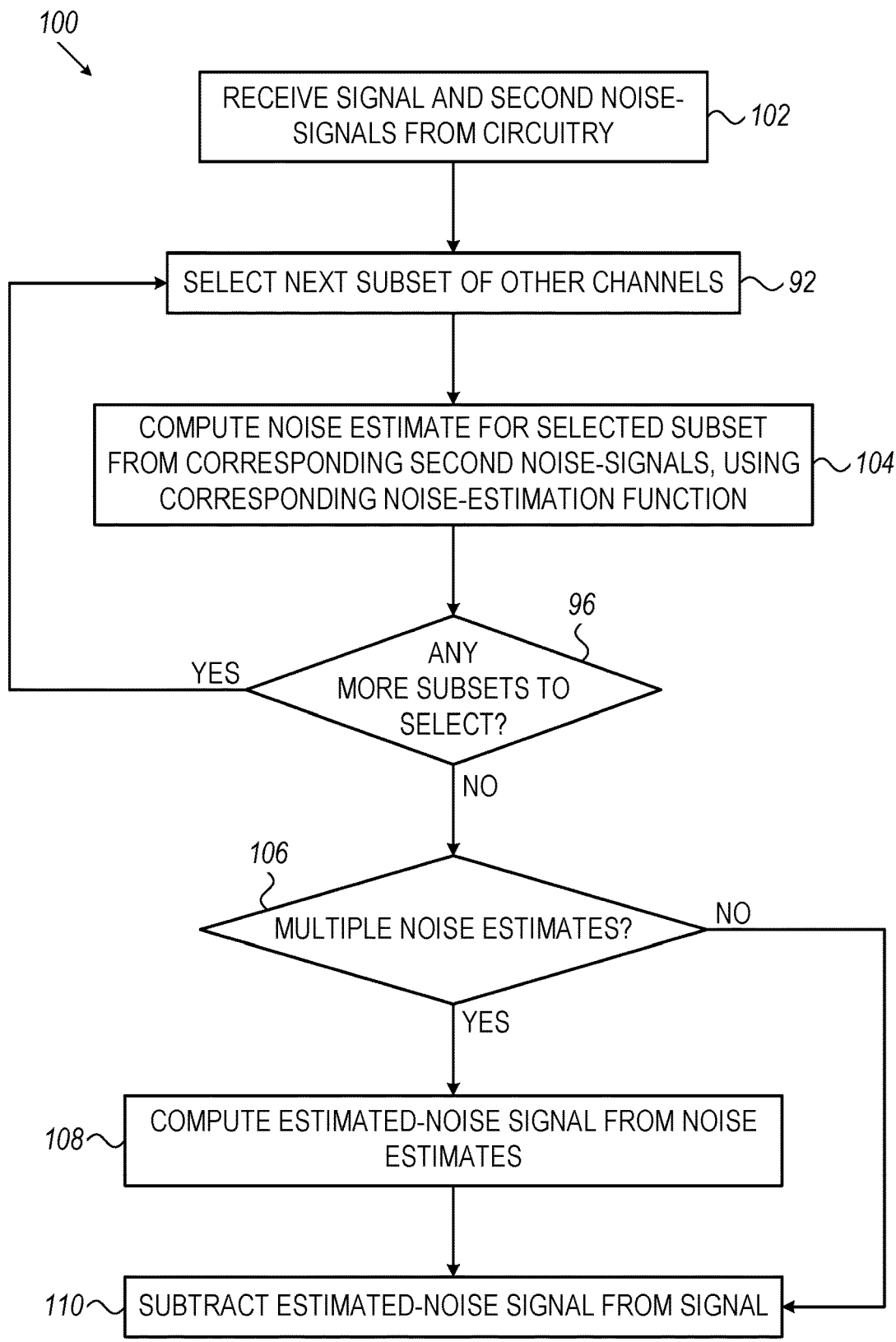
FIG. 6 is a flow diagram for an algorithm for reducing noise in a signal, in accordance with some examples of the present disclosure.

For an example implementation of this functionality, reference is now additionally made to FIG. 6, which is a flow diagram for an algorithm 100 for reducing noise in a signal, in accordance with some examples of the present disclosure.

Algorithm 100 begins with a signal-receiving step 102, at which the processor receives, from circuitry 47 (FIG. 1), signal 52 (FIG. 2), which was received over any given one of the channels, along with second noise-signals 60, which were received over one or more other channels while signal 52 was received. (As noted above, signal 52 and the second noise-signals may be received before the first noise-signals, i.e., signal-receiving step 102 may be executed before signal-receiving step 88 of FIG. 4.) Following signal-receiving step 102, the processor selects a subset of the other channels at subset-selecting step 92.

For each selected subset, the processor, at an estimate-computing step 104, computes a noise estimate for the selected subset from the corresponding second noise-signals, using the corresponding noise-estimation function. In other words, using the noise-estimation function that was computed for the selected subset and for the given channel, the processor computes an estimate of the noise in signal 52 based on the second noise-signals that were received from the selected subset. Next, the processor checks, at checking step 96, whether any more subsets remain to be selected. If yes, the processor returns to subset-selecting step 92.

As noted above, in some examples, there is only a single subset of other channels, such that the processor computes only a single noise estimate from all of the second noise-signals. In other examples, the processor computes multiple noise estimates from different respective subsets of the second noise-signals, using different respective noise-estimation functions. For example, the processor may compute a separate noise estimate from each one of the second noise-signals.

Hence, upon ascertaining, at checking step 96, that no subsets remain to be selected, the processor checks, at another checking step 106, whether multiple noise estimates were computed. If yes, the processor computes estimated-noise signal 62 from the noise estimates at an estimated-noise-signal-computing step 108. For example, the processor may compute the estimated-noise signal by applying a median filter to the noise estimates. Otherwise, estimated-noise-signal-computing step 108 is omitted, given that the estimated-noise signal was already computed at estimate-computing step 104.

Following estimated-noise-signal-computing step 108, or if this step is omitted, the processor, at a subtracting step 110, subtracts estimated-noise signal 62 from signal 52, thereby obtaining less-noisy signal 52' (FIG. 2).

II. One-Stage Technique

In other examples, the processor uses only one set of noise-signals. In other words, to compute the estimated-noise signal, the processor applies the noise-estimation functions to the same noise-signals that were used to compute the noise-estimation functions. In such examples, typically, the noise-signals include, at most, only a small amount of ultrasound-reflection transduction. For example, for each of the noise-signals, the energy of the noise in the signal may exceed the energy of any ultrasound reflections in the signal, e.g., by a factor of at least five, such as a factor of at least ten.

Figure 7:
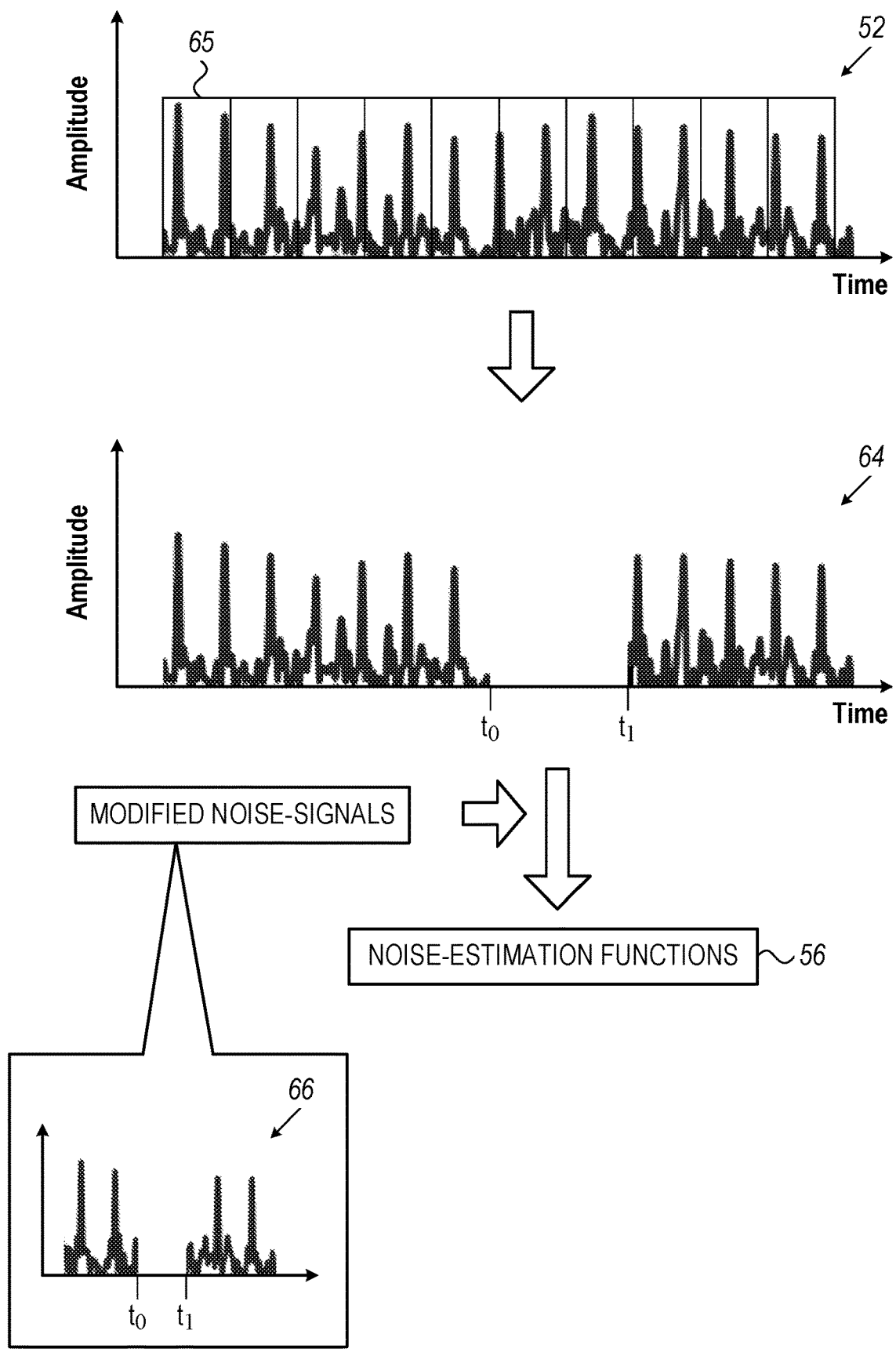
FIG. 7 is a schematic illustration of a computation of one or more noise-estimation functions, in accordance with some examples of the present disclosure.

For further details, reference is now made to FIG. 7, which is a schematic illustration of a computation of one or more noise-estimation functions 56, in accordance with some examples of the present disclosure.

In some examples, following the receipt of signal 52 over any given channel, the processor extracts a noise-signal 64 from signal 52. The processor then uses noise-signal 64, together with one or more noise-signals 66 that were received over respective other channels while signal 52 was received over the given channel, to compute one or more noise-estimation functions for the given channel.

For example, the processor may first segment signal 52 into multiple segments 65. Subsequently, the processor may identify one or more segments 65 that include less transduction of ultrasound reflections than do other segments, i.e., that are noisier than the other segments. Next, the processor may construct noise-signal 64 from the identified segments, e.g., by nullifying the unidentified (less-noisy) segments in signal 52.

Typically, prior to computing noise-estimation functions 56, the processor modifies noise-signals 66 by removing noise from any time windows in which signal 52 is not represented in noise-signal 64. For example, as shown in FIG. 7, if noise-signal 64 is null between t0 and t1, the processor may nullify the portion of each noise-signal 66 that runs from t0 to t1. Subsequently, the processor computes noise-estimation functions 56 based on the modified noise-signals 66 and noise-signal 64.

In some examples, to identify the noisier segments 65, the processor first computes a respective per-segment noise-estimation function for each segment 65, based on the corresponding portions of noise-signals 66. For example, if a particular segment runs from t2 to t3, the processor may compute the per-segment noise-estimation function based on the respective portions of noise-signals 66 running from t2 to t3. Subsequently, the processor clusters the per-segment noise-estimation functions, e.g., using the K-means algorithm or the density-based spatial clustering of applications with noise (DBSCAN) algorithm. (For example, if each per-segment noise-estimation function includes multiplication by an impulse-response vector as described below with reference to FIG. 9, the processor may cluster the impulse-response vectors.) Next, the processor identifies the segments corresponding to the largest cluster of per-segment noise-estimation functions.

Figure 8:
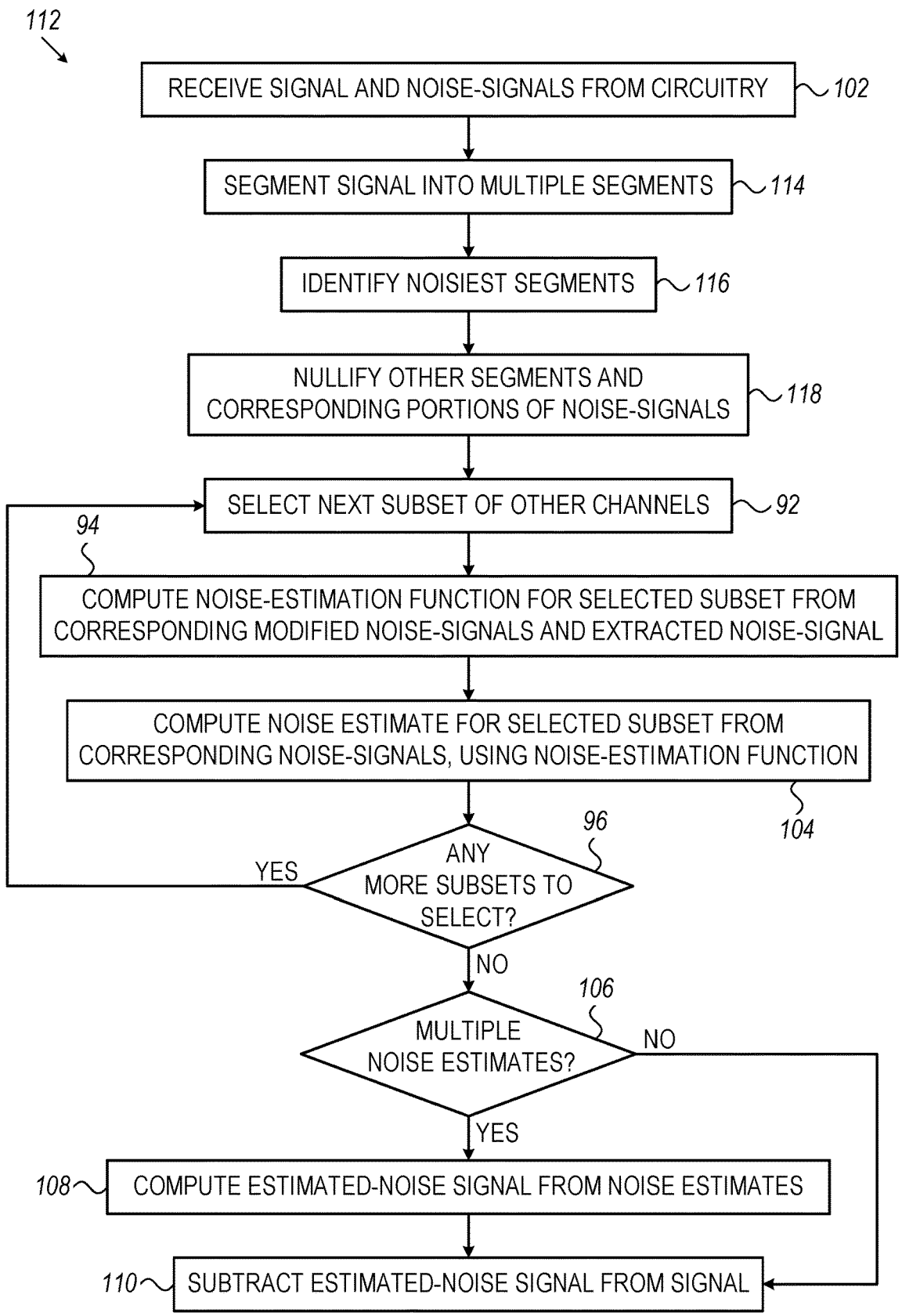
FIG. 8 is a flow diagram for an algorithm for removing noise from a signal, in accordance with some examples of the present disclosure.

Following the computation of noise-estimation functions 56, the processor applies the noise-estimation functions to the (unmodified) noise-signals so as to compute an estimated-noise signal. For an example implementation of the above-described functionality, reference is further made to FIG. 8, which is a flow diagram for an algorithm 112 for removing noise from a signal, in accordance with some examples of the present disclosure.

Algorithm 112 begins with signal-receiving step 102, at which the processor receives, from the circuitry, signal 52 (FIG. 2), which was received over any given one of the channels, and noise-signals 66, which were received over one or more other channels. Following signal-receiving step 102, the processor segments signal 52 into multiple segments at a segmenting step 114. Subsequently, at a segment-identifying step 116, the processor identifies the noisiest segments of the signal. Next, at a nullifying step 118, the processor nullifies the other (less-noisy) segments (thereby obtaining an extracted noise-signal) and the corresponding portions of noise-signals 66 (thereby obtaining modified noise-signals).

Next, each subset of other channels is selected at subset-selecting step 92. For each selected subset, the processor, at function-computing step 94, computes a noise-estimation function from the modified noise-signals corresponding to the subset and the extracted noise-signal. The processor then executes estimate-computing step 104 so as to compute a noise estimate from the corresponding (unmodified) noise-signals, using the noise-estimation function. Following estimate-computing step 104, the processor executes checking step 96.

Upon ascertaining, at checking step, that no more subsets remain to be selected, algorithm 112 continues as in algorithm 100 (FIG. 6).

Computing and Using the Noise-Estimation Functions

As described above, the processor is configured to compute one or more noise-estimation functions for any given channel, each such function being applicable to one or more noise-signals received over respective other channels so as to estimate the noise received over the given channel. In some examples, the processor computes the noise-estimation functions by computing respective impulse-response vectors, such that each noise-estimation function includes multiplication by an impulse-response vector.

Figure 9:
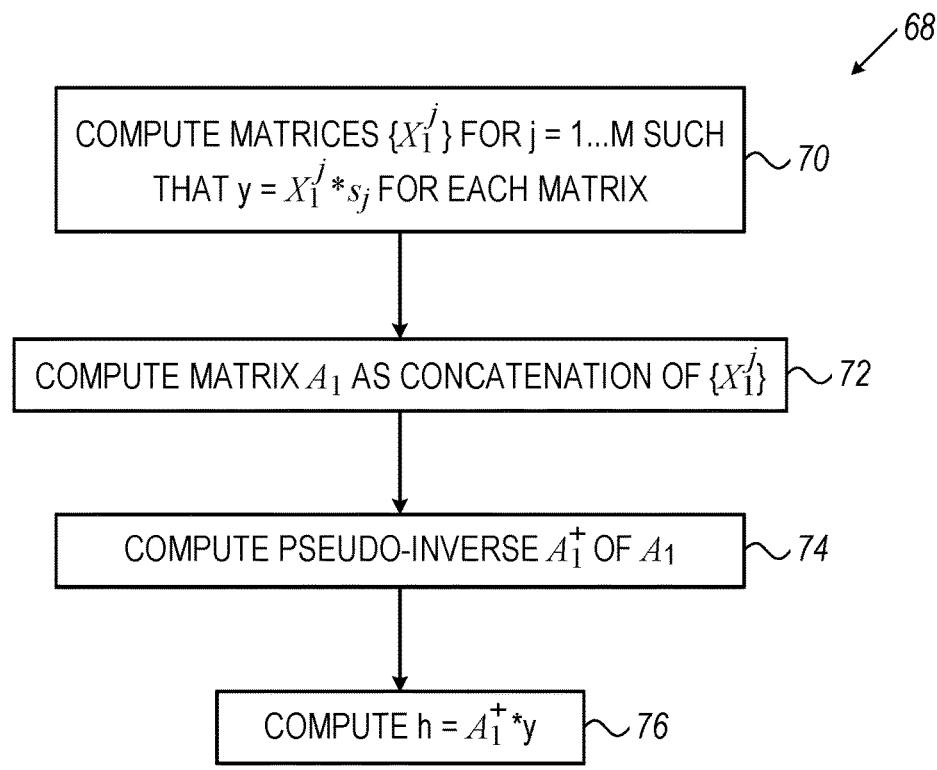
FIG. 9 is a flow diagram for an example computation of an impulse-response vector, in accordance with some examples of the present disclosure.
Figure 10:
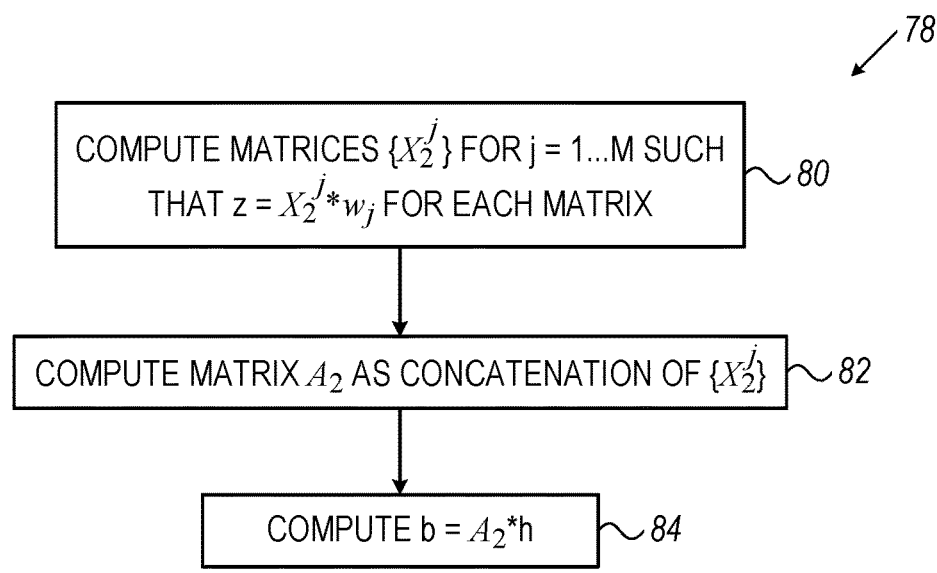
FIG. 10 is a flow diagram for an example computation of a noise estimate, in accordance with some examples of the present disclosure.

In this regard, reference is now made to FIG. 9, which is a flow diagram for an example computation 68 of an impulse-response vector, in accordance with some examples of the present disclosure. Computation 68 may be performed in the execution of function-computing step 94 of FIGS. 4 and 8. Reference is also made to FIG. 10, which is a flow diagram for an example computation 78 of a noise estimate, in accordance with some examples of the present disclosure. Computation 78 may be performed in the execution of estimate-computing step 104 of FIGS. 6 and 8.

Prior to describing FIGS. 9-10, the following notation is hereby introduced:

M is the number of noise-signals in the subset of noise-signals used to calculate the impulse-response vector (and hence, the noise-estimation function).

$s_j$, for j=1 ... M, is the $j^{th}$ noise-signal in the subset, which, for the one-stage technique, may be modified relative to the original $j^{th}$ noise-signal as described above with reference to FIG. 7.

y is a representation of noise received over the given channel while the noise-signals in the subset were received. In particular, for the two-stage technique, y is the first noise-signal 58 (FIG. 3) received over the given channel. For the one-stage technique, y is extracted noise-signal 64 (FIG. 7).

h is an impulse-response vector.

z is signal 52 (FIG. 2).

For the two-stage technique, $w_j$ is the $j^{th}$ second noise-signal 60 (FIG. 5), i.e., the second noise-signal received over the same channel over which $s_j$ was received. For the one-stage technique, $w_j$ is the original (unmodified) $j^{th}$ noise-signal in the subset.

b is a noise estimate.

(It is noted that each of $s_j$, y, z, $w_j$, and b is a vector.)

Per FIG. 9, computation 68 begins with a matrix-computation step 70, at which the processor computes matrices $\{X_1^j\}$ for j=1 ... M such that, for each of the matrices, $y = X_1^j * s_j$. Next, at a concatenating step 72, the processor computes another matrix $A_1$ as the concatenation of $\{X_1^j\}$, i.e., the processor computes $A_1$ such that $A_1 = [X_1^1 \ X_1^2 \ \ldots \ X_1^M]$. Next, at a pseudo-inverse-computing step 74, the processor computes a pseudo-inverse $A_1^+$ of $A_1$; for example, $A_1^+$ may be the Moore-Penrose pseudo-inverse of $A_1$, i.e., $(A_1^T A_1)^{-1} A_1^T$. Finally, at an impulse-response-computing step 76, the processor computes $h = A_1^+ * y$.

With reference to FIG. 10, computation 78 begins with another matrix-computing step 80, at which the processor computes matrices $\{X_2^j\}$ for j=1 ... M such that, for each of the matrices, $z = X_2^j * w_j$. Subsequently, at another concatenating step 82, the processor computes another matrix $A_2$ as the concatenation of $\{X_2^j\}$, i.e., the processor computes $A_2$ such that $A_2 = [X_2^1 \ X_2^2 \ \ldots \ X_2^M]$. Finally, at an impulse-response-applying step 84, the processor computes $b = A_2 * h$.

In some examples, respective signals are received (at different respective times) over N channels, and for each of the N channels, the removal of noise is based on respective noise-signals received over the N−1 other channels. In such examples, the processor may compute the impulse-response vectors for all of the channels at once, in the form of an impulse-response matrix. (Thus, rather than performing function-computing 94 step separately for each channel as shown in FIG. 4, the processor may perform a single function-computing step for all of the channels.) Using the impulse-response matrix, the processor may remove noise from all of the signals at once, rather than removing noise from each signal individually. (Thus, rather than performing estimate-computing step 104 separately for each given channel as shown in FIG. 6, the processor, after receiving the signal and second noise-signals for all of the channels, may perform a single estimate-computing step for all of the channels.)

For further details, the following notation is introduced:

$$S = \begin{pmatrix} s_1 \\ s_2 \\ \vdots \\ s_N \end{pmatrix},$$

where $s_j$, for j=1 ... N, is the first noise-signal 58 (FIG. 3) received over the $j^{th}$ channel. (S is thus of size N×L, L being the length, in samples, of each first noise-signal.)

$X_1^{j,k}$, for j=1 ... N, k=1 ... N, and j≠k, is the matrix for which $s_j = X_1^{j,k} * s_k$.

$$B_1 = \begin{pmatrix} A_1^1 & 0 & \cdots & 0 \\ 0 & A_1^2 & \ddots & \vdots \\ \vdots & \ddots & \ddots & 0 \\ 0 & \cdots & 0 & A_1^N \end{pmatrix},$$

where $A_1^j$, for j=1 ... N, is the concatenation of $\{X_1^{j,k}\}$.

$$Z = \begin{pmatrix} z_1 \\ z_2 \\ \vdots \\ z_N \end{pmatrix},$$

where $z_j$, for j=1 ... N, is the signal received over the $j^{th}$ channel. (Z is thus of size N×L.)

$w_{j,k}$ is the $k^{th}$ second noise-signal received while $z_j$ was received.

$X_2^{j,k}$, for j=1 ... N, k=1 ... N, and j≠k, is the matrix for which $z_j = X_2^{j,k} * w_{j,k}$.

$$B_2 = \begin{pmatrix} A_2^1 & 0 & \cdots & 0 \\ 0 & A_2^2 & \ddots & \vdots \\ \vdots & \ddots & \ddots & 0 \\ 0 & \cdots & 0 & A_2^N \end{pmatrix},$$

where $A_2^j$, for j=1 ... N, is the concatenation of $\{X_2^{j,k}\}$.

First, the processor may compute $B_1^+$, a pseudo-inverse (e.g., the Moore-Penrose pseudo-inverse) of $B_1$. Next, the processor may compute the impulse-response matrix $$H = B_1^+ * S = \begin{pmatrix} A_1^{1+} & 0 & \cdots & 0 \\ 0 & A_1^{2+} & \ddots & \vdots \\ \vdots & \ddots & \ddots & 0 \\ 0 & \cdots & 0 & A_1^{N+} \end{pmatrix} * \begin{pmatrix} s_1 \\ s_2 \\ \vdots \\ s_N \end{pmatrix} = \begin{pmatrix} h_1 \\ h_2 \\ \vdots \\ h_N \end{pmatrix},$$

where $h_1 \ldots h_N$ are the respective impulse-response vectors for the N channels. The processor may further compute an estimated-noise matrix as $$B_2 * H = \begin{pmatrix} A_2^1 & 0 & \cdots & 0 \\ 0 & A_2^2 & \ddots & \vdots \\ \vdots & \ddots & \ddots & 0 \\ 0 & \cdots & 0 & A_2^N \end{pmatrix} * \begin{pmatrix} h_1 \\ h_2 \\ \vdots \\ h_N \end{pmatrix} = \begin{pmatrix} A_2^1 * h_1 \\ A_2^2 * h_2 \\ \vdots \\ A_2^N * h_N \end{pmatrix},$$

and then subtract this matrix from Z.

Optimizations

Figure 11:
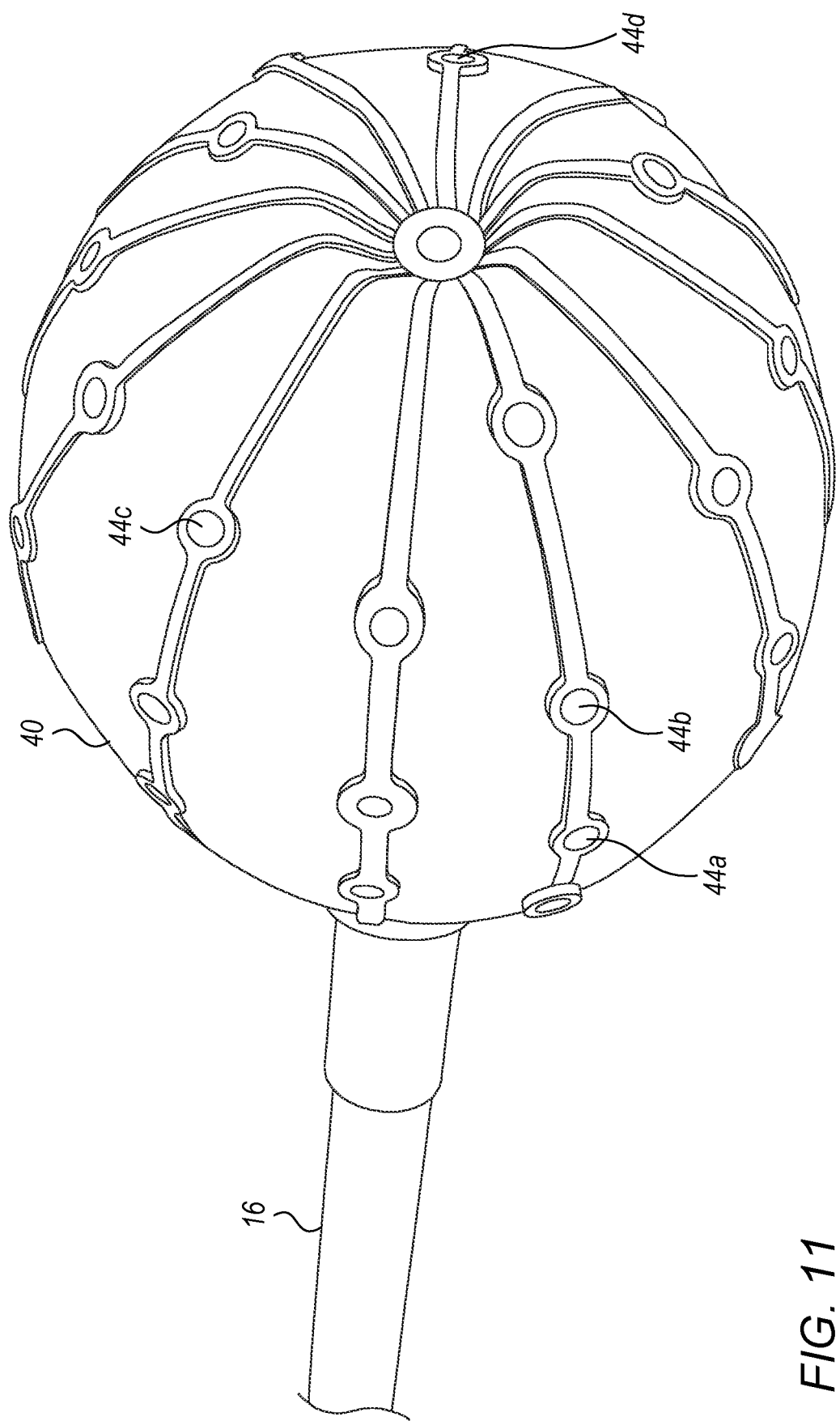
FIG. 11 is a schematic illustration of an ultrasound catheter, in accordance with some examples of the present disclosure.

Reference is now made to FIG. 11, which is a schematic illustration of ultrasound catheter 16, in accordance with some examples of the present disclosure.

In some examples, the removal of noise from a given channel does not rely on all of the other channels, but rather, only on a group of other channels that does not include all of the other channels. For example, those channels connected to ultrasound transducers that are closer to the ultrasound transducer connected to the given channel may be excluded from the group, on account of being likely to carry a greater amount of reflection of ultrasound waves transmitted by the ultrasound transducer connected to the given channel. Thus, for example, each of the ultrasound transducers connected to any one of the channels in the group may be farther from the ultrasound transducer connected to the given channel than is at least one 4 ultrasound transducers connected to any one of the channels not in the group.

For example, by virtue of ultrasound transducer 44b being relatively close to ultrasound transducer 44a, ultrasound transducer 44b may receive and transduce reflections of ultrasound waves transmitted by ultrasound transducer 44a, i.e., it may be difficult or impossible to receive a noise-signal over the channel of (i.e., the channel that is connected to) ultrasound transducer 44b while a signal is received over the channel of ultrasound transducer 44a. Hence, the group of channels used to remove noise from the channel of ultrasound transducer 44a may exclude the channel of ultrasound transducer 44b. On the other hand, the group may include the channel of another ultrasound transducer 44c, which is farther from ultrasound transducer 44a.

Alternatively or additionally, the channels of those ultrasound transducers that are relatively far from the ultrasound transducer connected to the given channel may be excluded from the group. For example, the channel of another ultrasound transducer 44d may be excluded from the group for the channel of ultrasound transducer 44a.

In such examples, for greater efficiency, a signal may be received over the given channel, and/or noise-signals used for removing noise from the given channel may be received from the group of other channels, while another signal, which includes a transduction of ultrasound reflections, is received over at least one of the channels that is not in the group.

For example, for the computation of a noise-estimation function for the channel of ultrasound transducer 44a, respective first noise-signals may be received over the channels of ultrasound transducer 44a and ultrasound transducer 44c. While these noise-signals are received, a signal may be received over the channel of ultrasound transducer 44d, which is not in the group of other channels for the channel of transducer 44a.

As another example, while a signal is received over the channel of ultrasound transducer 44a and a noise-signal (e.g., a second noise-signal for the two-stage technique) is received over the channel of ultrasound transducer 44c, another signal may be received over the channel of ultrasound transducer 44b and/or the channel of ultrasound transducer 44d, each of which is not in the group of other channels for the channel of transducer 44a.

Alternatively or additionally, for greater efficiency, the processor may cause at least one of the ultrasound transducers connected to one of the channels in the group to transmit ultrasound waves differently from the ultrasound transducer connected to the given channel. For example, the two ultrasound transducers may transmit with different frequencies, e.g., using orthogonal frequency-division multiplexing. Circuitry 47 (FIG. 1) may thus receive another signal, which includes a transduction of reflections of the ultrasound waves, over the channel. The processor may then separate noise from this other signal, based on the difference in transmission. The processor may then reduce noise in the signal received over the given channel based on the separated noise.

For example, the processor may cause ultrasound transducer 44a to transmit with a frequency f1, and ultrasound transducer 44c to transmit with a frequency f2. The processor may then separate noise at frequency f1 from a signal received over the channel of transducer 44c, and use this separated noise to learn a noise-estimation function for, or to compute an estimated-noise signal for, the channel of ultrasound transducer 44a. Similarly, the processor may separate noise at frequency f2 from a signal received over the channel of ultrasound transducer 44a (optionally while another signal is received over the channel of ultrasound transducer 44c), and use this separated noise to learn a noise-estimation function for, or to compute an estimated-noise signal for, the channel of ultrasound transducer 44c.

EXAMPLES

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It s also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A system (10) for use with multiple ultrasound transducers (44) disposed on a catheter (16) and connected to different respective channels (49) includes circuitry (47) and a processor (48). The circuitry is configured to receive a signal (52), which includes a transduction (54) of ultrasound reflections, over any given one of the channels, and to receive respective noise-signals (58), which include less transduction of ultrasound reflections than does the signal, over a group of others of the channels. The processor is configured to receive the signal and the noise-signals from the circuitry, and to reduce noise in the signal, by, based on the noise-signals, computing one or more noise-estimation functions (56) for the given channel, each of the noise-estimation functions being applicable to a respective subset of the noise-signals so as to return an estimate of noise received over the given channel while the subset of the noise-signals were received, using the noise-estimation functions, computing an estimated-noise signal (62), and subtracting the estimated-noise signal from the signal.

Example 2

The system (10) according to Example 1,
wherein the circuitry (47) is configured to receive the signal (52) while receiving the noise-signals (58),
wherein the processor (48) is configured to compute the noise-estimation functions (56) by:
extracting another noise-signal (64) from the signal, and
computing the noise-estimation functions based on the received noise-signals (58) and the extracted noise-signal, and
wherein the processor is configured to compute the estimated-noise signal (62) by applying the noise-estimation functions to the received noise-signals.

Example 3

The system (10) according to Example 2, wherein the processor (48) is configured to extract the other noise-signal (64) by:
segmenting the signal into multiple segments (65),
identifying one or more of the segments that include less transduction of ultrasound reflections than do others of the segments, and
constructing the other noise-signal from the identified segments.

Example 4

The system (10) according to Example 1,
wherein the noise-signals are first noise-signals (58),
wherein the circuitry (47) is configured to receive the signal (52) before or after receiving the first noise-signals,
wherein the circuitry is further configured to:
while receiving the first noise-signals, receive another first noise-signal, which includes less transduction of ultrasound reflections than does the signal, over the given channel, and
while receiving the signal, receive respective second noise-signals (60) over the group of others of the channels,
wherein the processor is further configured to receive the other first noise-signal and the second noise-signals from the circuitry,
wherein the processor (48) is configured to compute the noise-estimation functions (56) based on the first noise-signals and on the other first noise-signal, and
wherein the processor is configured to compute the estimated-noise signal (62) by applying the noise-estimation functions to the second noise-signals.

Example 5

The system (10) according to any one of Examples 1-4, wherein the processor (48) is configured to compute the noise-estimation functions (56) by computing respective impulse-response vectors.

Example 6

The system (10) according to Example 5, wherein the processor (48) is configured to compute each of the impulse-response vectors by:
computing matrices $\{X_1^j\}$ for j=1 . . . M, M being a number of the noise-signals (58) in the subset for the impulse-response vector, such that, for each of the matrices, $y = X_1^j * s_j$, y being a representation of noise received over the given channel while the noise-signals in the subset were received, and $s_j$ being a $j^{th}$ one of the noise-signals in the subset;

computing another matrix $A_1$ as a concatenation of $\{X_1^j\}$, computing a pseudo-inverse $A_1^+$ of $A_1$, and computing the impulse-response vector as $A_1^{+}*y$.

Example 7

The system (10) according to Example 5, wherein the processor (48) is configured to compute the estimated-noise signal (62) by computing respective noise estimates for the impulse-response vectors, by, for each of the impulse-response vectors:

computing matrices $\{X_2^j\}$ for j=1 . . . M, M being a number of the noise-signals (58) in the subset for the impulse-response vector, such that, for each of the matrices, $z=X_2^j*w_j$, z being the signal (52), and $w_j$ being a $j^{th}$ one of the noise-signals in the subset or another noise-signal (60) received, while receiving the signal, over the channel over which the $j^{th}$ noise-signal was received, computing another matrix $A_2$ as a concatenation of $\{X_2^j\}$, and computing the noise estimate for the impulse-response vector by multiplying the impulse-response vector by $A_2$.

Example 8

The system (10) according to any one of Examples 1-7, wherein the group does not include all others of the channels (49).

Example 9

The system (10) according to Example 8, wherein each of the ultrasound transducers (44) connected to any one of the channels (49) in the group is farther from the ultrasound transducer connected to the given channel than is at least one of the ultrasound transducers connected to any one of the channels not in the group.

Example 10

The system (10) according to any one of Examples 8-9, wherein the circuitry (47) is configured to receive the noise-signals (58) while receiving another signal, which includes another transduction of ultrasound reflections, over at least one of the channels (49) that is not in the group.

Example 11

The system (10) according to any one of Examples 8-10, wherein the circuitry (47) is configured to receive the signal (52) while receiving another signal, which includes another transduction of ultrasound reflections, over at least one of the channels (49) that is not in the group.

Example 12

The system (10) according to any one of Examples 1-11, wherein the processor (48) is further configured to cause at least one of the ultrasound transducers (44) connected to one of the channels (49) in the group to transmit ultrasound waves differently from the ultrasound transducer connected to the given channel, wherein the circuitry (47) is further configured to receive another signal, which includes a transduction of reflections of the ultrasound waves, over the channel in the group, wherein the processor is further configured to:
receive the other signal from the circuitry, and
separate noise from the other signal, based on the difference in transmission, and wherein the processor is configured to reduce the noise in the signal (52) based on the separated noise.

Example 13

The system (10) according to any one of Examples 1-12, wherein the one or more noise-estimation functions (56) consist of a single noise-estimation function, which is applicable to all of the noise-signals (58).

Example 14

The system (10) according to any one of Examples 1-12, wherein the one or more noise-estimation functions (56) include multiple noise-estimation functions, and wherein the processor (48) is configured to compute the estimated-noise signal (62) by:

using the noise-estimation functions (56), computing respective noise estimates, and computing the estimated-noise signal from the noise estimates.

Example 15

A method for use with multiple ultrasound transducers (44) disposed on a catheter (16) and connected to different respective channels (49) includes receiving a signal (52), which includes a transduction (54) of ultrasound reflections, over any given one of the channels. The method further includes receiving respective noise-signals (58), which include less transduction of ultrasound reflections than does the signal, over a group of others of the channels. The method further includes reducing noise in the signal, by, based on the noise-signals, computing one or more noise-estimation functions (56) for the given channel, each of the noise-estimation functions being applicable to a respective subset of the noise-signals so as to return an estimate of noise received over the given channel while the subset of the noise-signals were received, using the noise-estimation functions, computing an estimated-noise signal (62), and subtracting the estimated-noise signal from the signal.

It will be appreciated by persons skilled in the art that the present disclosure is not limited to what has been particularly shown and described hereinabove. Rather, the scope of the present disclosure includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system for use with multiple ultrasound transducers disposed on a catheter and connected to different respective channels, the system comprising:
   circuitry, configured to:
      receive a signal, which includes a transduction of ultrasound reflections, over any given one of the channels, and
      receive respective noise-signals, which include less transduction of ultrasound reflections than does the signal, over a group of others of the channels; and
   a processor, configured to:
      receive the signal and the noise-signals from the circuitry, and
      reduce noise in the signal, by:
         based on the noise-signals, computing one or more noise-estimation functions for the given channel by extracting another noise-signal from the signal and computing the noise-estimation functions based on the received noise-signals and the extracted noise-signal, each of the noise-estimation functions being applicable to a respective subset of the noise-signals so as to return an estimate of noise received over the given channel while the subset of the noise-signals were received,
         using the noise-estimation functions, computing an estimated-noise signal by applying the noise-estimation functions to the received noise-signals, and
         subtracting the estimated-noise signal from the signal.

2. The system according to claim 1, wherein the processor is configured to extract the other noise-signal by:
   segmenting the signal into multiple segments,
   identifying one or more of the segments that include less transduction of ultrasound reflections than do others of the segments, and
   constructing the other noise-signal from the identified segments.

3. The system according to claim 1,
   wherein the noise-signals are first noise-signals,
   wherein the circuitry is configured to receive the signal before or after receiving the first noise-signals,
   wherein the circuitry is further configured to:
      while receiving the first noise-signals, receive another first noise-signal, which includes less transduction of ultrasound reflections than does the signal, over the given channel, and
      while receiving the signal, receive respective second noise-signals over the group of others of the channels,
   wherein the processor is further configured to receive the other first noise-signal and the second noise-signals from the circuitry,
   wherein the processor is configured to compute the noise-estimation functions based on the first noise-signals and on the other first noise-signal, and
   wherein the processor is configured to compute the estimated-noise signal by applying the noise-estimation functions to the second noise-signals.

4. The system according to claim 1, wherein the processor is configured to compute the noise-estimation functions by computing respective impulse-response vectors.

5. The system according to claim 4, wherein the processor is configured to compute each of the impulse-response vectors by:
   computing matrices $\{X_1^j\}$ for $j=1 \ldots M$, M being a number of the noise-signals in the subset for the impulse-response vector, such that, for each of the matrices, $y = X_1^j * s_j$,
      y being a representation of noise received over the given channel while the noise-signals in the subset were received, and
      $s_j$ being a $j^{th}$ one of the noise-signals in the subset;
   computing another matrix $A_1$ as a concatenation of $\{X_1^j\}$,
   computing a pseudo-inverse $A_1^+$ of $A_1$, and
   computing the impulse-response vector as $A_1^{+**} y$.

6. The system according to claim 4, wherein the processor is configured to compute the estimated-noise signal by computing respective noise estimates for the impulse-response vectors, by, for each of the impulse-response vectors:
   computing matrices $\{X_2^j\}$ for $j=1 \ldots M$, M being a number of the noise-signals in the subset for the impulse-response vector, such that, for each of the matrices, $z = X_2^j * w_j$,
      z being the signal, and
      $w_j$ being a $j^{th}$ one of the noise-signals in the subset or another noise-signal received, while receiving the signal, over the channel over which the $j^{th}$ noise-signal was received, computing another matrix $A_2$ as a concatenation of $\{X_2^j\}$, and
   computing the noise estimate for the impulse-response vector by multiplying the impulse-response vector by $A_2$.

7. The system according to claim 1, wherein the group does not include all others of the channels.

8. The system according to claim 7, wherein each of the ultrasound transducers connected to any one of the channels in the group is farther from the ultrasound transducer connected to the given channel than is at least one of the ultrasound transducers connected to any one of the channels not in the group.

9. The system according to claim 7, wherein the circuitry is configured to receive the noise-signals while receiving another signal, which includes another transduction of ultrasound reflections, over at least one of the channels that is not in the group.

10. The system according to claim 7, wherein the circuitry is configured to receive the signal while receiving another signal, which includes another transduction of ultrasound reflections, over at least one of the channels that is not in the group.

11. The system according to claim 1,
   wherein the processor is further configured to cause at least one of the ultrasound transducers connected to one of the channels in the group to transmit ultrasound waves differently from the ultrasound transducer connected to the given channel,
   wherein the circuitry is further configured to receive another signal, which includes a transduction of reflections of the ultrasound waves, over the channel in the group,
   wherein the processor is further configured to:
      receive the other signal from the circuitry, and
      separate noise from the other signal, based on the difference in transmission, and
   wherein the processor is configured to reduce the noise in the signal based on the separated noise.

12. The system according to claim 1, wherein the one or more noise-estimation functions consist of a single noise-estimation function, which is applicable to all of the noise-signals.

13. The system according to claim 1, wherein the one or more noise-estimation functions include multiple noise-estimation functions, and wherein the processor is configured to compute the estimated-noise signal by:
- using the noise-estimation functions, computing respective noise estimates, and
- computing the estimated-noise signal from the noise estimates.

14. A method for use with multiple ultrasound transducers disposed on a catheter and connected to different respective channels, the method comprising:
- receiving a signal, which includes a transduction of ultrasound reflections, over any given one of the channels;
- receiving respective noise-signals, which include less transduction of ultrasound reflections than does the signal, over a group of others of the channels; and
- reducing noise in the signal, by:
  - based on the noise-signals, computing one or more noise-estimation functions for the given channel by extracting another noise-signal from the signal and computing the noise-estimation functions based on the received noise-signals and the extracted noise-signal, each of the noise-estimation functions being applicable to a respective subset of the noise-signals so as to return an estimate of noise received over the given channel while the subset of the noise-signals were received,
  - using the noise-estimation functions, computing an estimated-noise signal, and
  - subtracting the estimated-noise signal from the signal.

15. The method according to claim 14, wherein extracting the other noise-signal comprises:
- segmenting the signal into multiple segments;
- identifying one or more of the segments that include less transduction of ultrasound reflections than do others of the segments; and
- constructing the other noise-signal from the identified segments.

16. The method according to claim 14,
wherein the noise-signals are first noise-signals,
wherein receiving the signal comprises receiving the signal before or after receiving the first noise-signals,
wherein the method further comprises:
- while receiving the first noise-signals, receiving another first noise-signal, which includes less transduction of ultrasound reflections than does the signal, over the given channel; and
- while receiving the signal, receiving respective second noise-signals over the group of others of the channels,
wherein computing the noise-estimation functions comprises computing the noise-estimation functions based on the first noise-signals and on the other first noise-signal, and
wherein computing the estimated-noise signal comprises computing the estimated-noise signal by applying the noise-estimation functions to the second noise-signals.

17. The method according to claim 14, wherein computing the noise estimation functions comprises computing the noise-estimation functions by computing respective impulse-response vectors.

18. The method according to claim 17, wherein computing each of the impulse-response vectors comprises:
- computing matrices $\{X_1^j\}$ for $j=1\ldots M$, M being a number of the noise-signals in the subset for the impulse-response vector, such that, for each of the matrices, $y=X_1^j*s_j$,
  - y being a representation of noise received over the given channel while the noise-signals in the subset were received, and
  - $s_j$ being a $j^{th}$ one of the noise-signals in the subset;
- computing another matrix $A_i$ as a concatenation of $\{X_1^j\}$;
- computing a pseudo-inverse $A_1^+$ of $A_1$; and
- computing the impulse-response vector as $A_1^{+}*y$.

19. The method according to claim 17, wherein computing the estimated-noise signal comprises computing respective noise estimates for the impulse-response vectors, by, for each of the impulse-response vectors:
- computing matrices $\{X_2^j\}$ for $j=1\ldots M$, M being a number of the noise-signals in the subset for the impulse-response vector, such that, for each of the matrices, $z=X_2^j*w_j$,
  - z being the signal, and
  - $w_j$ being a $j^{th}$ one of the noise-signals in the subset or another noise-signal received, while receiving the signal, over the channel over which the $j^{th}$ noise-signal was received,
- computing another matrix $A_2$ as a concatenation of $\{X_2^j\}$, and
- computing the noise estimate for the impulse-response vector by multiplying the impulse-response vector by $A_2$.

20. The method according to claim 14, wherein the group does not include all others of the channels.

21. The method according to claim 20, wherein each of the ultrasound transducers connected to any one of the channels in the group is farther from the ultrasound transducer connected to the given channel than is at least one of the ultrasound transducers connected to any one of the channels not in the group.

22. The method according to claim 20, wherein receiving the noise-signals comprises receiving the noise-signals while receiving another signal, which includes another transduction of ultrasound reflections, over at least one of the channels that is not in the group.

23. The method according to claim 20, wherein receiving the signal comprises receiving the signal while receiving another signal, which includes another transduction of ultrasound reflections, over at least one of the channels that is not in the group.

24. The method according to claim 14, further comprising:
- causing at least one of the ultrasound transducers connected to one of the channels in the group to transmit ultrasound waves differently from the ultrasound transducer connected to the given channel;
- receiving another signal, which includes a transduction of reflections of the ultrasound waves, over the channel in the group; and
- separating noise from the other signal, based on the difference in transmission,
wherein reducing the noise in the signal comprises reducing the noise in the signal based on the separated noise.

25. The method according to claim 14, wherein the one or more noise-estimation functions consist of a single noise-estimation function, which is applicable to all of the noise-signals.

26. The method according to claim 14, wherein the one or more noise-estimation functions include multiple noise-estimation functions, and wherein computing the estimated-noise signal comprises:
- using the noise-estimation functions, computing respective noise estimates; and computing the estimated-noise signal from the noise estimates.

* * * * *